US008343128B2

(12) United States Patent
Nagao et al.

(10) Patent No.: US 8,343,128 B2

(45) Date of Patent: Jan. 1, 2013

(54) MULTIPLE-CHAMBER MEDICAL CONTAINER AND BAG FOR ENCLOSING SAME

(75) Inventors: Katsuyoshi Nagao, Tokushima (JP); Toshiharu Yokoyama, Tokushima (JP); Keiichi Kawakami, Tokushima (JP)

(73) Assignee: Otsuka Pharmaceutical Factory, Inc., Naruto-shi (JP)

(*) Notice: Subject to any disclaimer, the term of this patent is extended or adjusted under 35 U.S.C. 154(b) by 1135 days.

(21) Appl. No.: 10/509,673

(22) PCT Filed: Apr. 25, 2003

(86) PCT No.: PCT/JP03/05327

§ 371 (c)(1), (2), (4) Date: Oct. 8, 2004

(87) PCT Pub. No.: WO03/092574

PCT Pub. Date: Nov. 13, 2003

(65) Prior Publication Data

US 2005/0177128 A1 Aug. 11, 2005

(30) Foreign Application Priority Data

Apr. 30, 2002 (JP) ................................. 2002-128336
Aug. 7, 2002 (JP) ................................. 2002-229704
Feb. 17, 2003 (JP) ................................. 2003-38927

(51) Int. Cl.
*A61B 19/00* (2006.01)
*A61M 5/32* (2006.01)

(52) U.S. Cl. ......................... 604/410; 604/408; 604/416

(58) Field of Classification Search .................... 604/85, 604/87, 403–416; 206/219, 527, 222
See application file for complete search history.

(56) References Cited

U.S. PATENT DOCUMENTS

| | | | | |
|---|---|---|---|---|
| 3,255,872 A | | 6/1966 | Long et al. | |
| 4,602,910 A | * | 7/1986 | Larkin | 604/87 |
| 4,787,754 A | * | 11/1988 | Herrington | 383/63 |
| 5,423,421 A | * | 6/1995 | Inoue et al. | 206/219 |
| 5,425,447 A | * | 6/1995 | Farina | 206/219 |
| 5,458,244 A | * | 10/1995 | Emori | 206/527 |
| 5,462,526 A | * | 10/1995 | Barney et al. | 604/85 |

(Continued)

FOREIGN PATENT DOCUMENTS

EP 0 639 364 A 2/1995

(Continued)

OTHER PUBLICATIONS

Japanese Office Action mailed on Feb. 7, 2007. Japanese Office Action dated Aug. 15, 2007, with English translation.

*Primary Examiner* — Philip R Wiest
(74) *Attorney, Agent, or Firm* — Kratz, Quintos & Hanson, LLP

(57) ABSTRACT

A multiple-chamber medical container 1 comprises a container body 5 having two chambers 9, 11 for containing medicaments therein and a partitioning weak seal portion 13 for separating the chambers 9, 11 from each other, a medicinal outlet portion 7 attached to the container body 5 for discharging the medicaments from the chambers therethrough, and an openable small container 15 disposed in the first chamber 9 and having a medicament enclosed therein, the partitioning seal portion 15 being openable so as to cause the chambers 9, 11 to communicate with each other for use. The small container 15 can be opened by opening the partitioning weak seal portion 13.

23 Claims, 14 Drawing Sheets

U.S. PATENT DOCUMENTS

| | | | | | |
|---|---|---|---|---|---|
| 5,501,887 | A * | 3/1996 | Tanaka et al. | 428/35.2 |
| 6,036,004 | A * | 3/2000 | Bowen | 206/219 |
| 6,186,998 | B1 * | 2/2001 | Inuzuka et al. | 604/410 |
| 6,232,128 | B1 * | 5/2001 | Iguchi et al. | 436/163 |
| 6,319,243 | B1 * | 11/2001 | Becker et al. | 604/518 |
| 6,996,951 | B2 * | 2/2006 | Smith et al. | 53/425 |
| 2004/0134802 | A1 * | 7/2004 | Inoue et al. | 206/219 |
| 2005/0087456 | A1 * | 4/2005 | Oka et al. | 206/219 |

FOREIGN PATENT DOCUMENTS

| | | |
|---|---|---|
| GB | 951 300 A | 3/1964 |
| JP | 38-18695 | 6/1963 |
| JP | 1-168473 | 11/1989 |
| JP | 06-014975 | 1/1994 |
| JP | 2001-37847 | 2/2001 |
| JP | 2001-187111 | 7/2001 |

* cited by examiner (a)

(b)

MULTIPLE-CHAMBER MEDICAL CONTAINER AND BAG FOR ENCLOSING SAME

TECHNICAL FIELD

The present invention relates to multiple-chamber medical containers for individually enclosing therein different kinds of unstable medicaments which would undergo changes with time when mixed together and which can be mixed together in an aseptic state without producing any extraneous matter by opening a seal portion for partitioning the chambers.

BACKGROUND OF THE INVENTION

Patients undergoing surgery of digestive organs are generally unable to orally receive nourishment and therefore usually subjected to intravenous hyperalimentation (IVH). For IVH, carbohydrates, amino acids and electrolytes serving as nutrients are usually given, whereas for example if glucose and amino acids are preserved as enclosed in a single container, the mixture becomes brown due to the so-called Maillard reaction. Accordingly, these different kinds of medicaments need to be contained separately. For this reason, medical containers having a plurality of chambers for enclosing such medicaments are introduced into wide use in recent years.

Such a medical container comprises two chambers, for example, for respectively enclosing a parenteral solution containing amino acids and a parenteral solution containing glucose, and a seal portion partitioning these chambers separately. The seal portion is so adapted as to usually close a space between the two chambers and to open the space for use. When one of the chambers is pressed for use, an increased internal pressure of the chamber opens the seal portion to mix the medicaments in the two chambers together. When a conduit is then connected to an outlet provided in the container, the medicinal mixture can be given to the patient.

When IVH is used over a long period of time, it has been pointed out that the patient suffers from deficiencies of trace elements or vitamins which are not contained in the parenteral composition. However, since vitamin preparations are low in stability, it has been difficult to incorporate the vitamin preparation into the parenteral composition for IVH. To resolve this problem, the present applicant has proposed a multiple-chamber container as disclosed in WO, A1 No. 99/39679. The proposed container has, in addition to the conventional structure described, a small container enclosing a vitamin preparation therein and provided inside one of the chambers. The small container can be opened by being pressed from outside. When the medical container is to be used, the seal portion is opened to mix together the medicaments in the two chambers, and the small container in the chamber is opened by being pressed from outside to mix the vitamin preparation with the mixture.

The construction described above nevertheless involves the necessity of opening the small container in addition to the opening of the seal portion, hence the problem of a cumbersome procedure. Especially busy places of medical services, such a cumbersome procedure often burdens the worker heavily.

An object of the present invention, which has been accomplished to overcome this problem, is to provide a medical container comprising a plurality of chambers and adapted to readily and reliably open a small container therein.

DISCLOSURE OF THE INVENTION

To resolve the foregoing problem, the present invention provides a multiple-chamber medical container, the container comprising a container body having the chambers for containing medicaments therein and a partitioning seal portion for separating the chambers from one another, a medicinal outlet portion attached to the container body for discharging the medicaments from the chambers therethrough, and an openable small container disposed in at least one of the chambers and having a medicament enclosed therein, the partitioning seal portion being openable so as to cause the chambers to communicate with one another for use. The small container can be opened by opening the partitioning seal portion.

Thus, the small container is so adapted that it can be opened by opening the partitioning seal portion. This eliminates the need to open the small container in addition to the opening of the partitioning seal portion. The small container can therefore be opened with ease reliably, consequently reducing the burden on the worker at the busy place of medical services.

The partitioning seal portion can be formed by bonding opposed inner wall surfaces of the container body separably, the small container being formed with a sheet material which is bonded to the opposed inner wall surfaces of the container body, the small container being openable in accordance with the separation of the inner wall surfaces caused by opening the partitioning seal portion.

The small container can be at least partly bonded to the inner wall surfaces within the partitioning seal portion or within the chamber. In the case where the small container is so bonded within the chamber, it is desirable that the distance between the small container and the partitioning seal portion be 0 to 50 mm. At this time, it is further desirable that the small container be heat-sealed at at least one portion of a peripheral edge thereof, the sealed portion being openable by an external force, a nonbonded portion of the small container inwardly of the sealed portion of the peripheral edge having a bonded portion bonded to the inner wall surfaces of the chamber.

The bonded portion of the small container can be provided by a plurality of bonded parts arranged with at least one nonbonded part positioned therebetween. Preferably, the above-mentioned at least one nonbonded part is provided in the vicinity of a center of the bonded portion.

The sheet material of the small container can comprise a multilayer film and the small container can be opened by delaminating the multilayer film. Preferably, the sheet material of the small container can comprise a multilayer film formed by laminating a plurality of resin layers having low miscibility with one another.

Alternatively, the sheet material of the small container is at least partly heat-sealed, and the sealed portion is made openable by an external force.

With the medical container described, the small container is disposed in at least one of the chambers, whereby the medicament can be accommodated in the chamber. Even if the medicament to be accommodated in the chamber is altered in quantity, the same container body of unalterd size is usable by using a small container of different size. Further if the medicament to be accommodated is susceptible to photodeterioration, there is no need to change the material of the entire container body, but the container body is made usable by changing only the material of the small container. The medicinal container is therefore available at a reduced production cost. The medical container can then be so designed that the medicinal outlet portion is connected to the chamber having the small container disposed therein.

The medical container described can further be provided with a discharge-control seal portion serving as an openable partition between the medicinal outlet portion and the chamber. If an attempt is made to discharge the medicament through the medicinal outlet portion in error, for example, before opening the partitioning seal portion, the flow of the medicament from the chamber can be blocked by the discharge-control seal portion, thus preventing the medicament from becoming discharged before mixing. This makes the worker to realize the proper method of using the medical container, further making it possible to discharge the medicaments only after mixing.

The present invention further provides a bag for enclosing therein at least one multiple-chamber medical container and described above. The bag is characterized in that the bonded portion of the small container is provided approximately in parallel to the partitioning seal portion, the medical container being folded along an edge of the bonded portion on one side thereof opposite to the partitioning seal portion before being placed into the bag.

BEST MODE OF CARRYING OUT THE INVENTION

Figure 1:
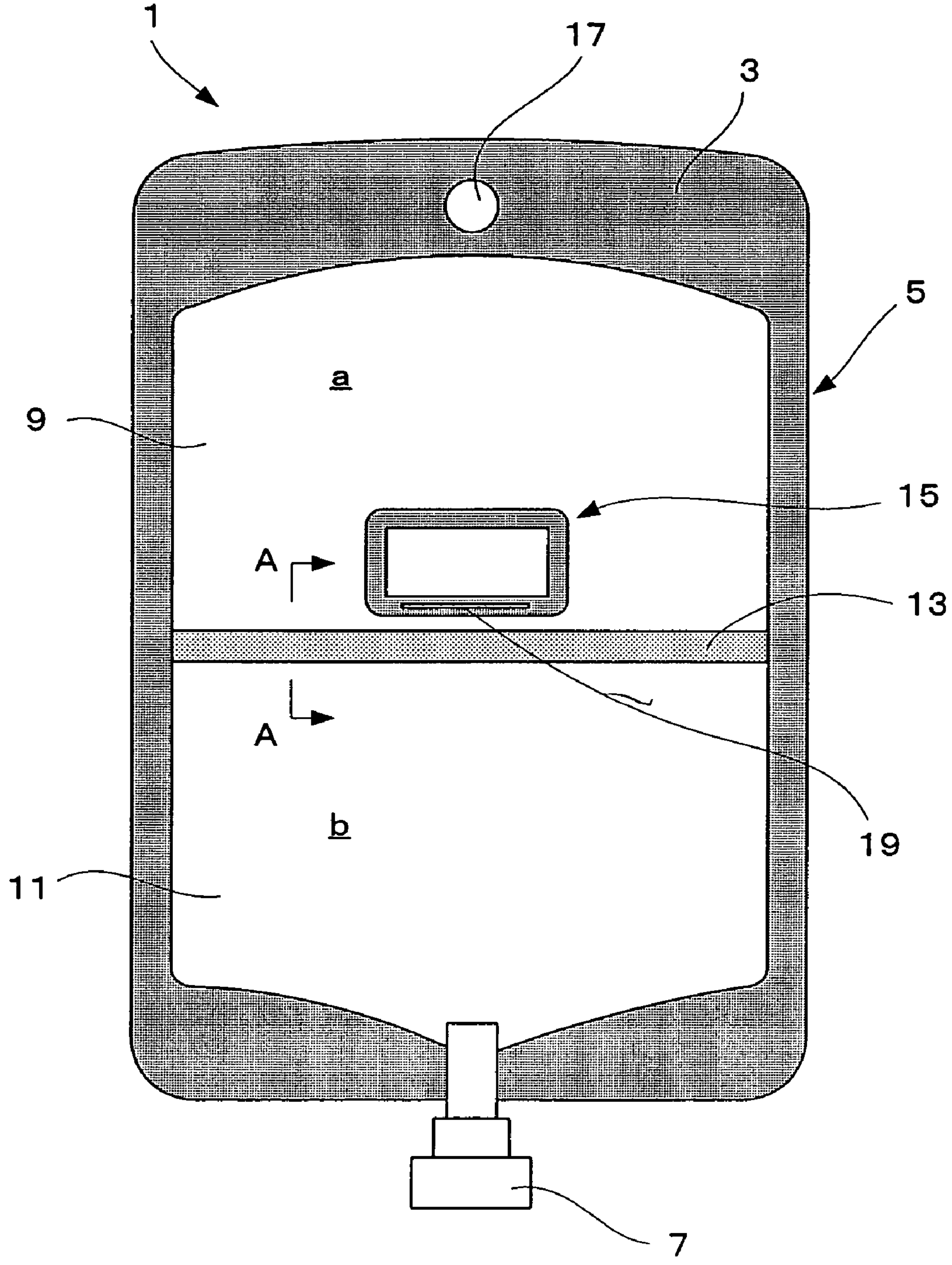
FIG. 1 is a plane view showing a first embodiment of multiple-chamber medical container according to the invention.

Multiple-chamber medical container and embodying the present invention will be described below with reference to the drawings. Throughout the embodiments, similar parts or like parts will be designated by like reference numerals and will not always be described repeatedly.

First Embodiment

A first embodiment of multiple-chamber medical container of the invention will be described first with reference to the drawings concerned. FIG. 1 is a plane view of a multiple-chamber medical container according to the first embodiment of the invention, and FIG. 2 includes views in section taken along the line A-A in FIG. 1.

As shown in FIG. 1, the medical container 1 comprises a rectangular container body 5 formed by heat-sealing two films along peripheral edge portions 3 thereof, and a medicinal outlet portion 7 joined to the container body 5 and having a rubber plug therein. The container body 5 has a first chamber 9 and a second chamber 11 which are arranged longitudinally thereof for enclosing medicaments therein. The two chambers 9, 11 are separated by a partitioning weak seal portion (partitioning seal portion) 13. The first chamber 9 has disposed therein a small container 15 containing a medicament therein as will be described later. The medicinal outlet portion 7 is connected to the second chamber 11. The end of the container body 5 opposite to the outlet portion 7 is provided with a suspending hole 17 for use in suspending the container 1.

The material of the films for the container body 5 can be any of various resin materials such as polyethylene, polypropylene, polystyrene and like thermoplastic resin. Usable is not only a film of single layer but a film of multilayer structure, such as a three-layer film comprising an inner layer and an outer layer of polyethylene, polypropylene or like polyolefin and an intermediate layer of cyclic olefin copolymer.

The partitioning weak seal portion 13 is formed by heat-sealing the two films of the container body 5 and extends in a direction approximately perpendicular to the longitudinal direction of the container body 5. The seal portion 13 is heat-sealed with such a strength as to usually separate the two chambers 9, 11 and to be opened for use by increasing the internal pressure of the chamber for use.

The chambers 9, 11 have accommodated therein respective different medicaments a, b which need to be separated because they undergo the Maillard reaction or like change with time when mixed together or made into a solution. For example, a solution containing amino acids can be placed in one of the chambers, and a solution containing a reducing sugar in the other chamber. Further when required, electrolytes or the like can be accommodated in one of the chambers. Not only such a solution, but also other powder or solid medicament can be accommodated in one of the chambers.

The small container 15 is in the form of a bag formed by heat-sealing the peripheral edges of two multilayer films (sheet material) and has a vitamin D solution enclosed therein. The multilayer film is a three-layer film which is susceptible to delamination and which can be prepared by sandwiching a cyclic olefin polymer layer between polyethylene layers. Also usable is a film which comprises an intermediate layer of resin having low miscibility with other resin layers and which is liable to delaminate, such as a film prepared by sandwiching a polypropylene layer between polyethylene layers. In this case, it is desirable that the innermost layer be 5 to 50 mm in thickness. In addition to the vitamin D solution, the medicament to be enclosed in the small container 15 can be selected from among a wide variety of medicaments which are undesirable to directly mix with the medicaments in the chambers 9, 11, such as powder or liquid medicaments of antibiotics, anticancer drugs or cardiotonic drugs. Although not limited particularly, the liquid medicaments usable include those of vitamins or trace elements, solutions such as physiological saline and glucose solution, and parenteral compositions.

Figure 2:
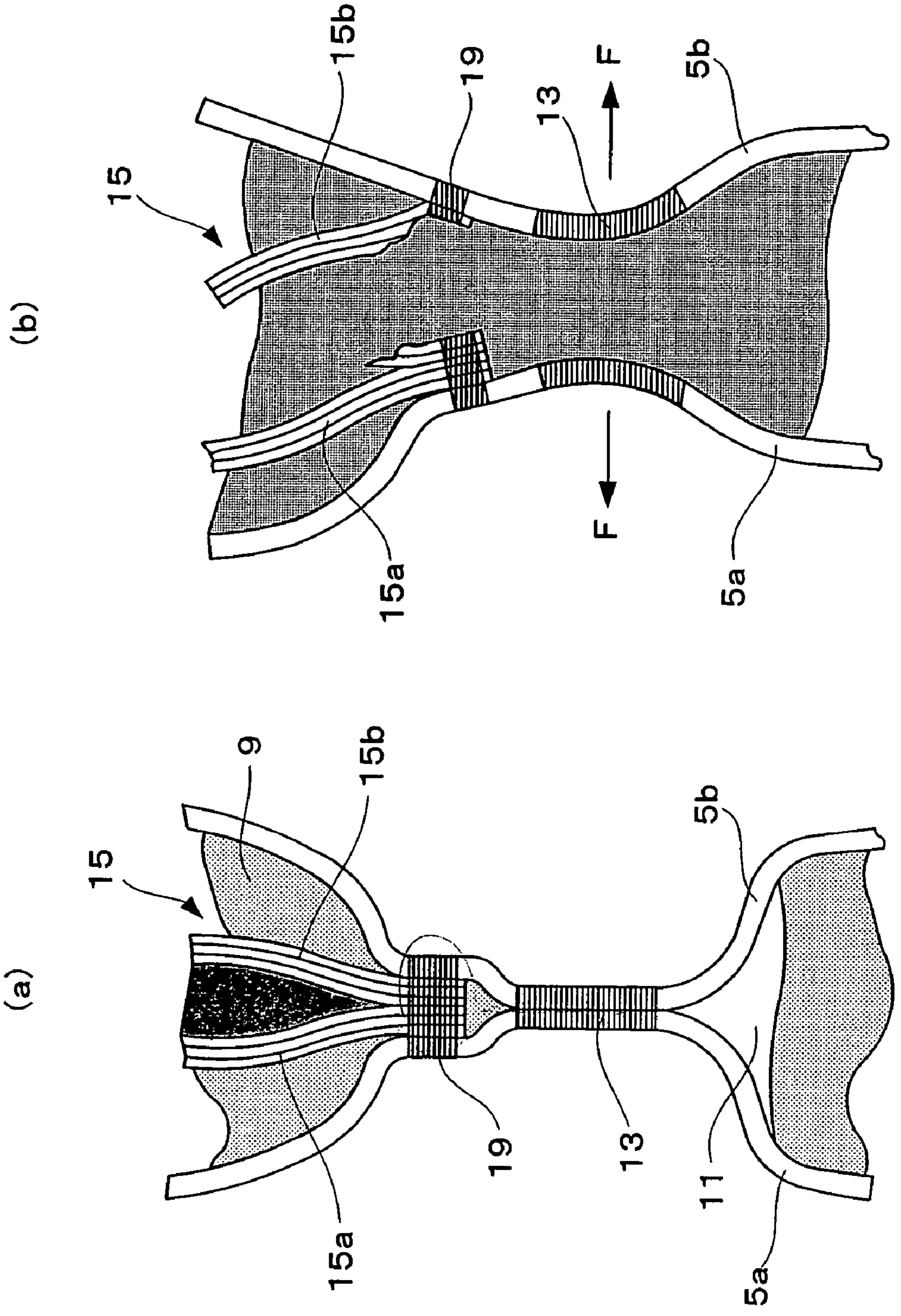
FIG. 2 includes views in section taken along the line A-A in FIG. 1.

As shown in FIG. 2(*a*). the small container 15 has one end heat-sealed to the inner wall surfaces of the films 5*a*, 5*b* forming the first chamber 9, and the heat-sealed portion provides a bonded portion 19. The bonded portion 19 is positioned about 10 mm away from the partitioning weak sealed portion 13, extends in parallel to the portion 13 and is thermally bonded with a strength higher than that of the weak seal portion 13 and usually not permitting separation of the bonded portion 19 like the peripheral edge portion 3 of the container body 5.

The multiple-chamber medical container and thus constructed will be used in the manner to be described next. To administer the medicaments within the container 1, the first or second chamber 9 or 11 is pressed as by manual pressing to increase the internal pressure of the chamber, whereby the partitioning weak seal portion 13 is opened to cause the first and second chambers 9, 11 to communicate with each other, mixing together the medicaments in the chambers 9, 11. The weak seal portion 13 is opened at this time by the separation of the films 5*a*, 5*b* of the container body 5, thereby opening the small container 15.

Stated more specifically with reference to FIG. 2(*b*), when the films 5*a*, 5*b* of the container body 5 separate, the resulting forces F act on the small container 15. Since the two multilayer films 15*a*, 15*b* of the small container 15 are fixed to the films 5*a*, 5*b* of the container body 5 by the bonded portion 19, the multilayer films 15*a*, 15*b* are separated along with the films 5*a*, 5*b* of the container body 5 at this time. As a result, one of the multilayer films 15*a*, 15*b* forming the small container 15 delaminates to rupture. In this way, the vitamin D solution enclosed in the small container 15 becomes mixed with the mixture of medicaments. The rubber plug of the medicinal outlet portion 7 is then pierced with a needle having a conduit (not shown) connected thereto, whereby the resulting mixture is administered to the patient through the conduit.

Thus according to the present embodiment, the multilayer films 15*a*, 15*b* forming the small container 15 are heat-sealed with a high strength to the inner wall surfaces of the first chamber 9 in the vicinity of the partitioning weak seal portion 13, so that the forces F for separating the films 5*a*, 5*b* of the container body 5 due to the opening of the weak seal portion 13 can be delivered to the small container 15 for the forces F to open the small container 15. This makes it possible to open the small container 15 with ease reliably while eliminating the need for an additional procedure for opening the small container 15 as conventionally practiced and consequently reducing the burden on the worker at the busy place of medical service.

Although the small container 15 is fixedly provided at a position 10 mm away from the partitioning weak seal portion accordingly the present embodiment, the small container 15 need not always be so positioned but can be positioned as desired. However, it is desired that the small container be positioned at a distance of 0 to 50 mm, more preferably 3 to 10 mm, from the weak seal portion 13 so that the forces to separate the films 5*a*, 5*b* of the container body 5 can be efficiently delivered to the small container when the weak seal portion 13 is opened. Furthermore, the small container 15 can be positioned as partly inserted into the partitioning weak seal portion 13.

Figure 3:
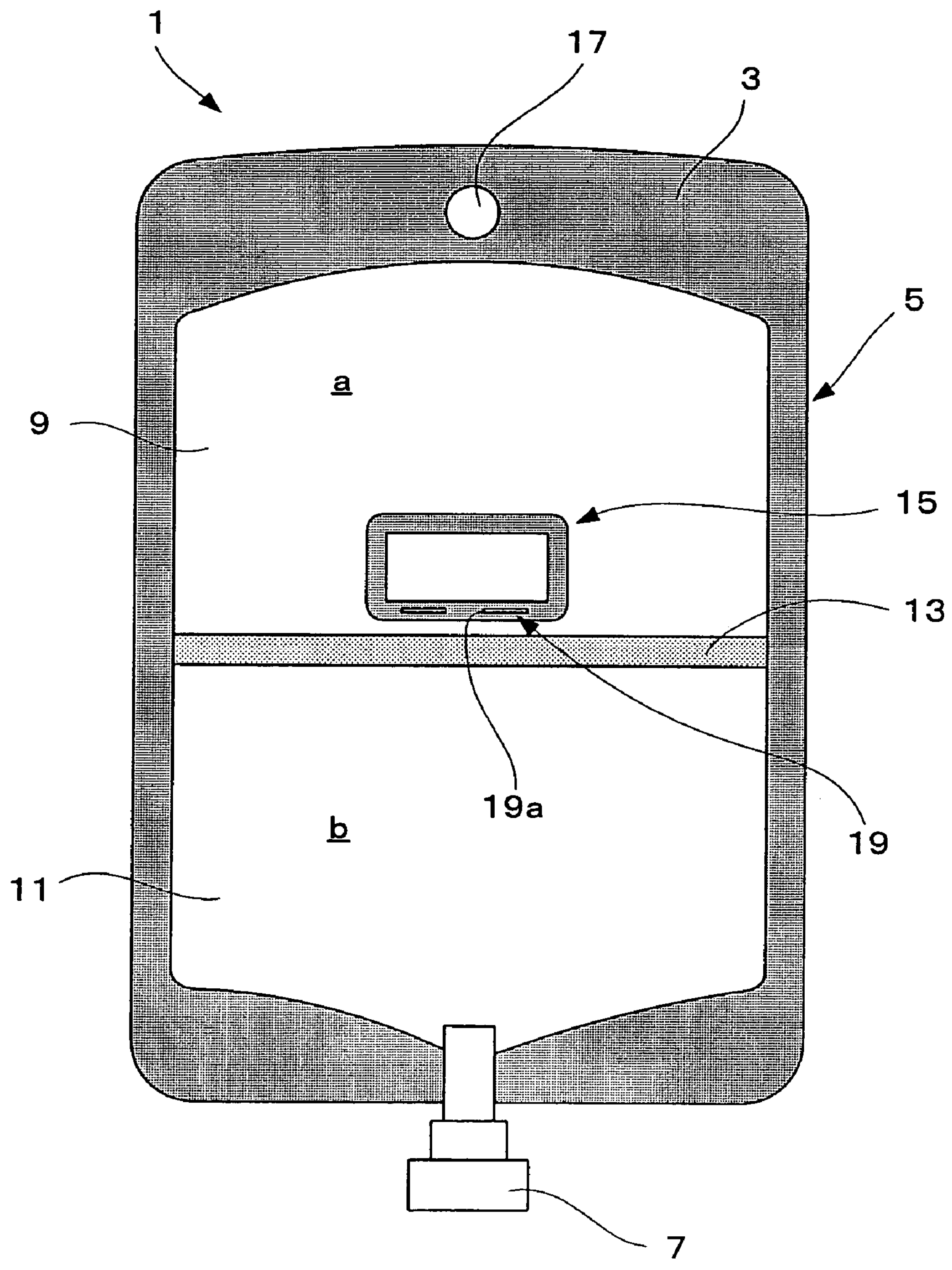
FIG. 3 is a plane view showing another example of multiple-chamber medical container of FIG. 1.

Further as shown in FIG. 3, a nonbonded part 19*a* where the small container 15 is not bonded to the inner wall surfaces can be provided at an intermediate part of the bonded portion 19. In the case where a pressure inadvertently applied to the container body 5 acts on the bonded portion 19, this portion 19 can be relieved of the pressure through the nonbonded part 19*a*. This prevents the pressure from acting concentrically on the bonded portion 19. The bonded portion 19 may have a structure other than the one shown in FIG. 3 insofar as this portion 19 comprises a plurality of bonded parts arranged with at least one nonbonded part 19*a* positioned therebetween. The nonbonded part 19*a* is then provided preferably in the vicinity of the center of the bonded portion 19 on which the pressure is most likely to act.

Figure 4:
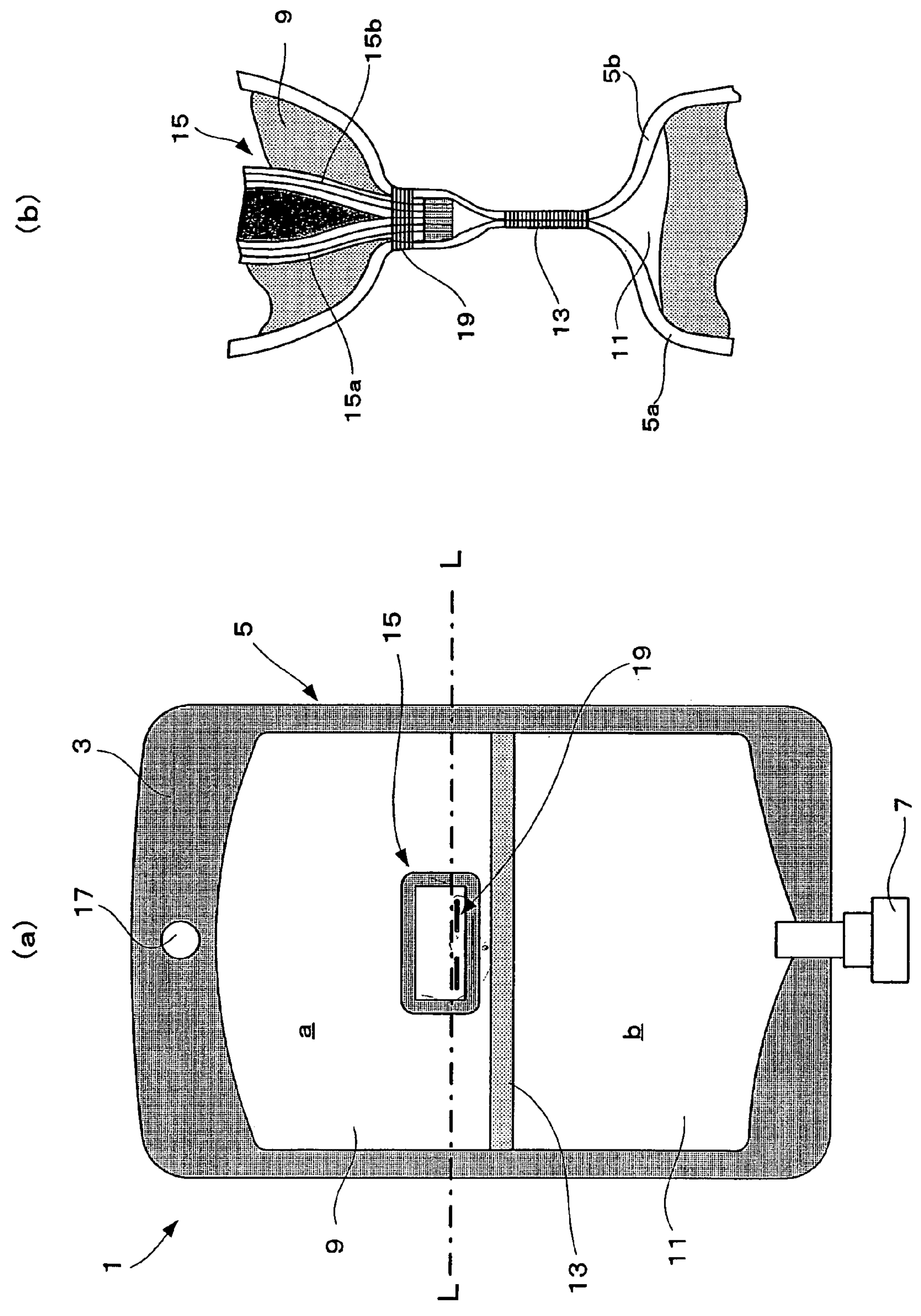
FIG. 4 is a plane view showing another example of multiple-chamber medical container of FIG. 1.

The bonded portion 19 is formed in the heat-sealed peripheral edge portion of the small container 15 according to the present embodiment. Since the small container 15 is then subjected to double heat sealing, the peripheral edge of the small container 15 appears to exhibit an impaired strength or appears liable to break. For this reason, the bonded portion 19 can be formed at a position inwardly of the peripheral edge of the small container 15 where the small container is not heat-sealed to bond the small container 15 to the container body 5 as shown in FIG. 4.

Figure 5:
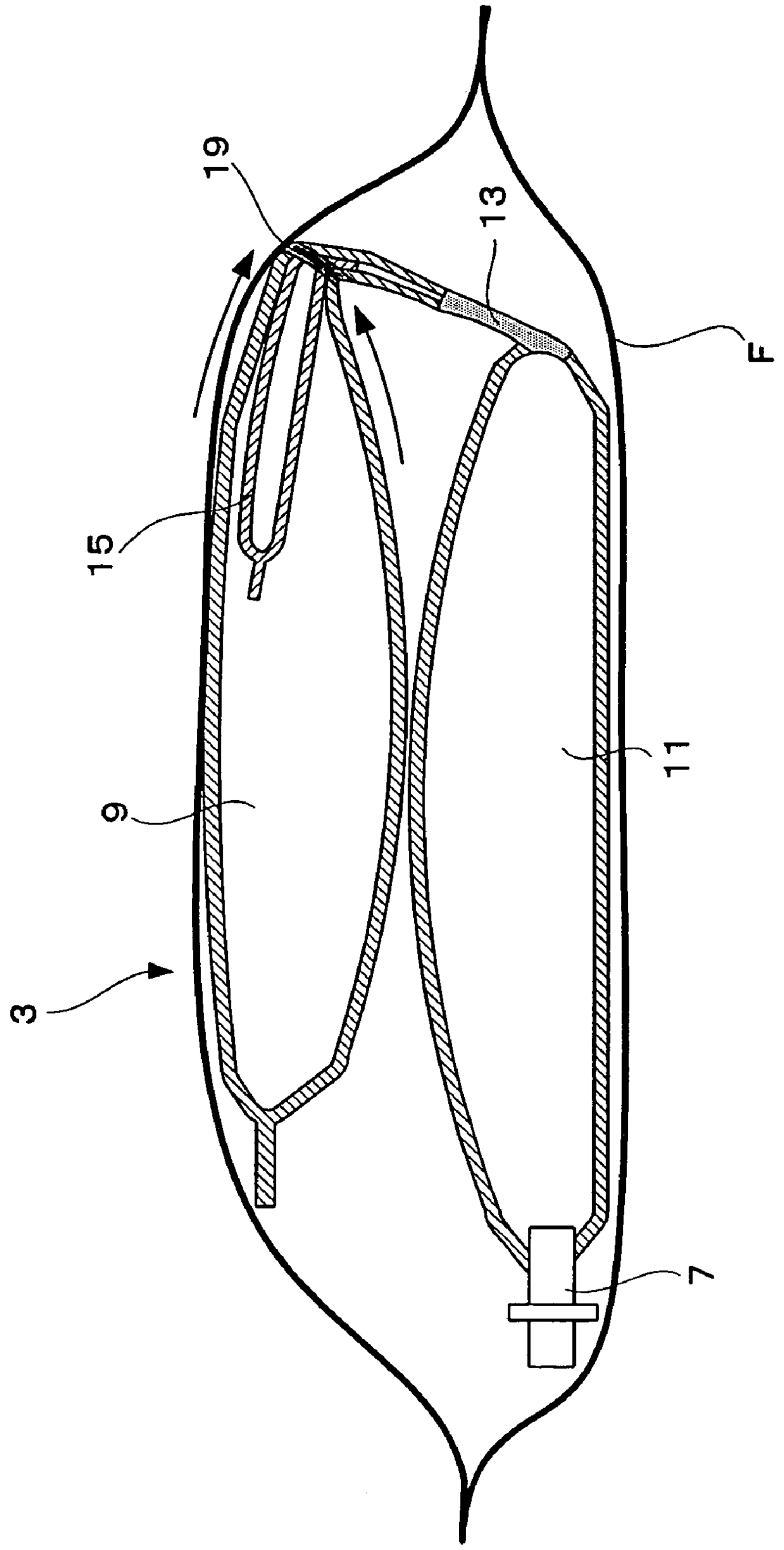
FIG. 5 is a view in section and showing the medical container of FIG. 1 as folded in two.

The multiple-chamber medical container 1 is transported usually as folded in two and placed in a bag. Accordingly, the bonded portion 19 provided at the specified position for fixedly bonding the small container 15 by heat sealing has the following advantages. The bonded portion 19 is provided in parallel to the partitioning weak seal portion 13 as shown in FIG. 5. Therefore, container 1 will be so folded that the first chamber 9 is positioned up, with the bonded portion 19 serving as a fold for folding the container 1 in two and disposed at one end of the folded container 1. Even if the first chamber 9 is then pressed and thereby given an increased internal pressure, the force resulting from this pressure and to be delivered to the weak seal portion 13 is blocked by the bonded portion 19. Furthermore, folding the container 1 in two at the bonded portion 19 serves to prevent the container body 5 from inflating in the vicinity of the bonded portion 19. Consequently, the above arrangement of the bonded portion 19 can prevent the weak seal portion 13 from opening even if the chamber having the small container 15 therein is pressed on during transport.

The bonded portion 19 providing a fold nevertheless has the likelihood that this portion 19 will break when subjected to a force produced by the folding of the component films. Accordingly, if the container 1 is folded in two along a line L shown in FIG. 4, i.e., along the upper edge of the bonded portion 19, the advantages described above are available, with the bonded portion 19 reliably prevented from breaking. Although one container 1 is shown as placed in the bag F in FIG. 5, at least two containers 1 can be placed into the bag.

Figure 6:
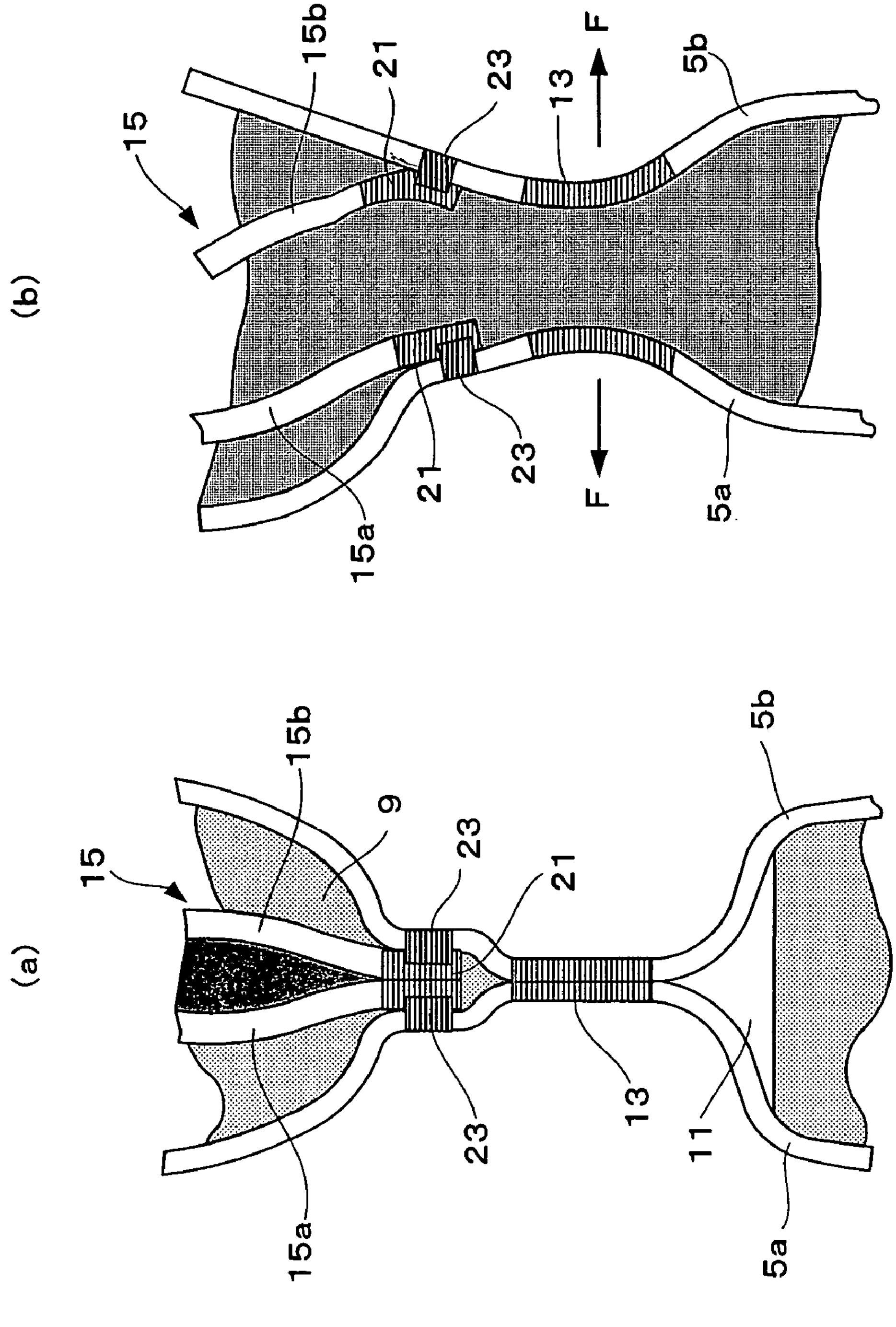
FIG. 6 includes fragmentary views in section and showing another example of multiple-chamber medical container of FIG. 1.

Further according to the present embodiment, the small chamber 15 is formed by the multilayer films 15*a*, 15*b* and made openable utilizing delamination, whereas single-layer films (sheet material) 15*a*, 15*b* can alternatively be used for attaching the small chamber to the container body in the following manner. With reference to FIG. 6(*a*), the peripheral edge portion of the small container 15 is partly made openable by forming a weak seal portion 21 as by heat sealing, and the outer surfaces of the films 15*a*, 15*b* forming the weak seal portion 21 are heat-sealed to the respective inner wall surfaces of the first chamber 9 to form bonded portions 23. At this time, care must be taken so as not to impart an increased opening strength to the weak seal portion 21 by giving the heat-sealing effect for forming the bonded portions 23 to the weak seal portion 21. Stated more specifically, only the outer surfaces of the weak seal portion 21 are heat-sealed to the inner wall surfaces of the first chamber 9. This structure permits the weak seal portion 21 also of the small container 15 to be opened by opening the partitioning weak seal portion 13 as shown in FIG. 6(*b*). The medicament in the small container 15 can therefore be mixed with the medicaments in the chambers reliably by a facilitated procedure. However, from the viewpoint of ease of fabrication, it is more preferable to use multilayer films because the films are liable to delaminate even if the films of the small chamber 15 is strongly heat-sealed throughout the combined thickness of the films.

The medical container described above can be fabricated by various processes, which include, for example, the following processes.

Figure 7:
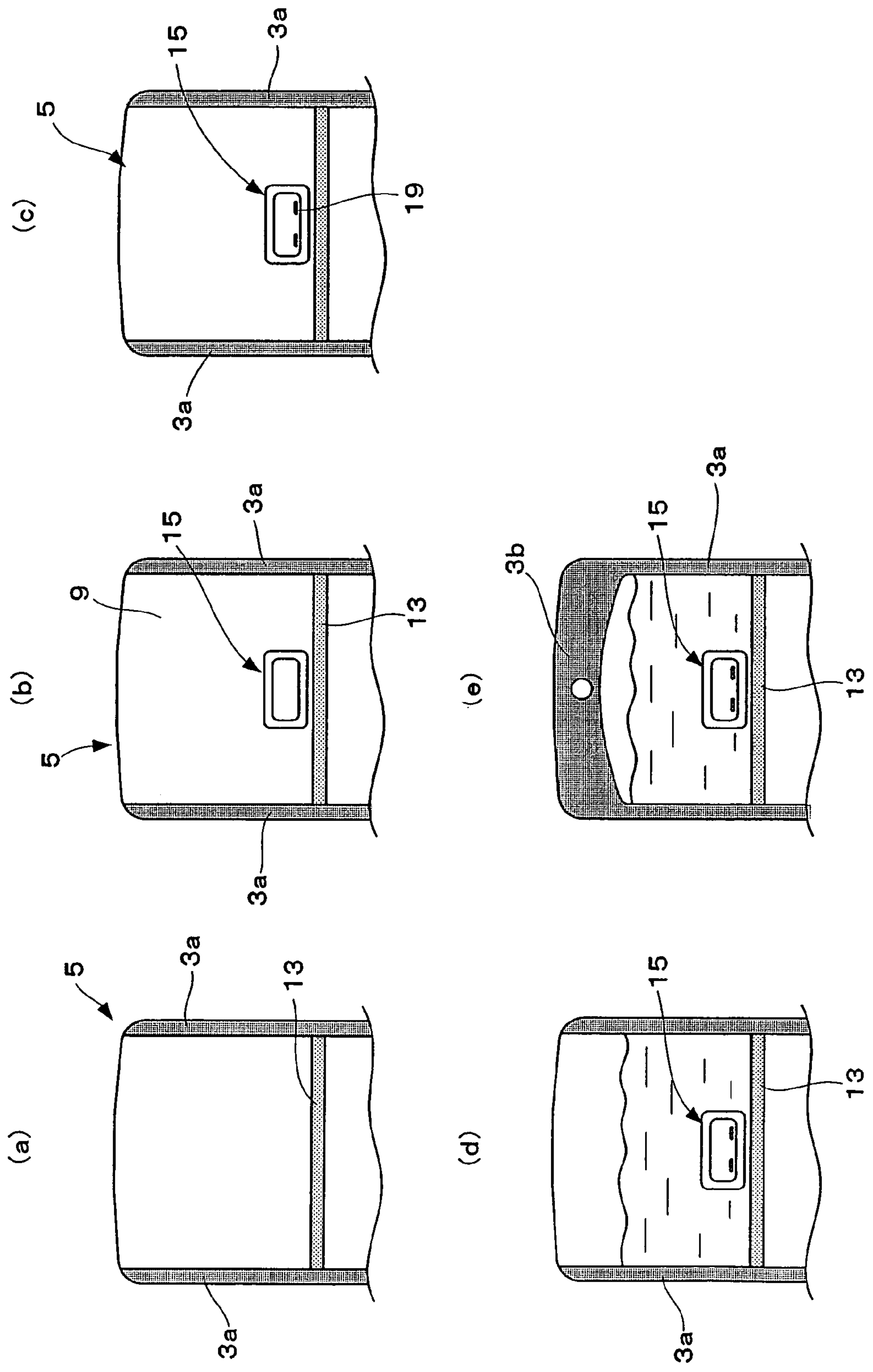
FIG. 7 includes views showing an exemplary process for producing the multiple-chamber medical container according to the invention.

With reference to FIG. 7, a container body is first strongly heat-sealed at opposite side portions of peripheral edge thereof to form strong seal portions 3*a*, and a partitioning weak seal portion 13 interconnecting the strong seal portions 3*a* is formed [FIG. 7(*a*)]. Subsequently, a small container 15 enclosing a medicament therein is placed into an upper chamber, i.e., a first chamber 9. At this time, the small container 15 is placed in as positioned close to the weak seal portion 13 [FIG. 7(*b*)]. A bonded portion 19 is then formed inwardly of the peripheral edge of the small container 15 to bond the small container 15 to the films forming the container body 5 [FIG. 7(*c*)]. The bonded portion 19 can be formed at a peripheral portion of the small container 15, i.e., at a heat-sealed portion thereof. A medicament is injected into the first chamber 9 through an opening at the upper end of the container body [FIG. 7(*d*)], and the first chamber 9 is thereafter sealed off by heat-sealing the upper end 3*b* of the container body 5 [FIG. 7(*e*)].

Figure 8:
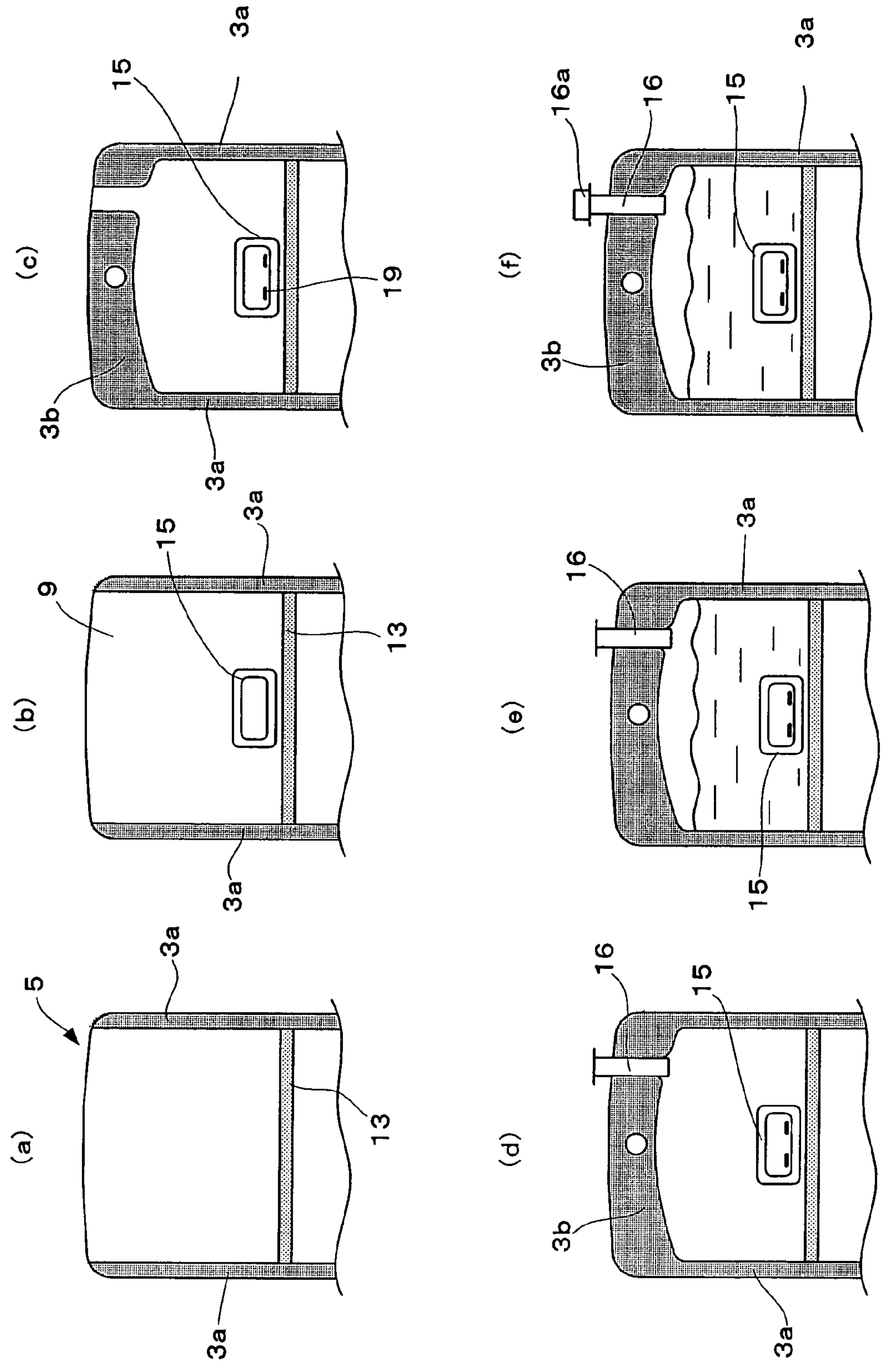
FIG. 8 includes views showing another exemplary process for producing the multiple-chamber medical container according to the invention.

With reference to FIG. 8, a port portion is alternatively formed in an upper end portion of the container body 5 to place in the medicament through the port portion. Stated more specifically, opposite-side strong seal portions 3*a* and a partitioning weak seal portion 13 are formed in a container body [FIG. 8(*a*)], and a small container 15 is placed into the first chamber 9 [FIG. 8(*b*)] and thereafter bonded to the container body in the same manner as above. The upper end 3*b* of the container body 5 is heat-sealed except for the part thereof for inserting the port portion therethrough [FIG. 8(*c*)]. Subsequently, the port portion 16 is inserted through the nonsealed part of the container body upper end 3*b*, and the port portion 16 is bonded to the upper end 3*b* by heat sealing [FIG. 8(*d*)]. A medicament is then injected into the first chamber 9 through the port portion 16 [FIG. 8(*e*)], and a plug 16*a* is fitted into the port portion 16 [FIG. 8(*f*)]. Alternatively, the medical container can be fabricated by placing in the medicament through the nonsealed part without attaching the port portion and thereafter heat-sealing this part.

As to the second chamber 11 formed by the above processes, a medicament can be placed in and a medicinal outlet portion 7 can be attached in the same manner as shown in FIGS. 8(*c*) to 8(*f*).

Second Embodiment

Next, a description will be given of a second embodiment of medical container comprising a plurality of chambers according to the invention. The second embodiment differs from the first in that a discharge-control weak seal portion is provided. Otherwise the present embodiment has the same construction, which therefore will not be described in detail.

Figure 9:
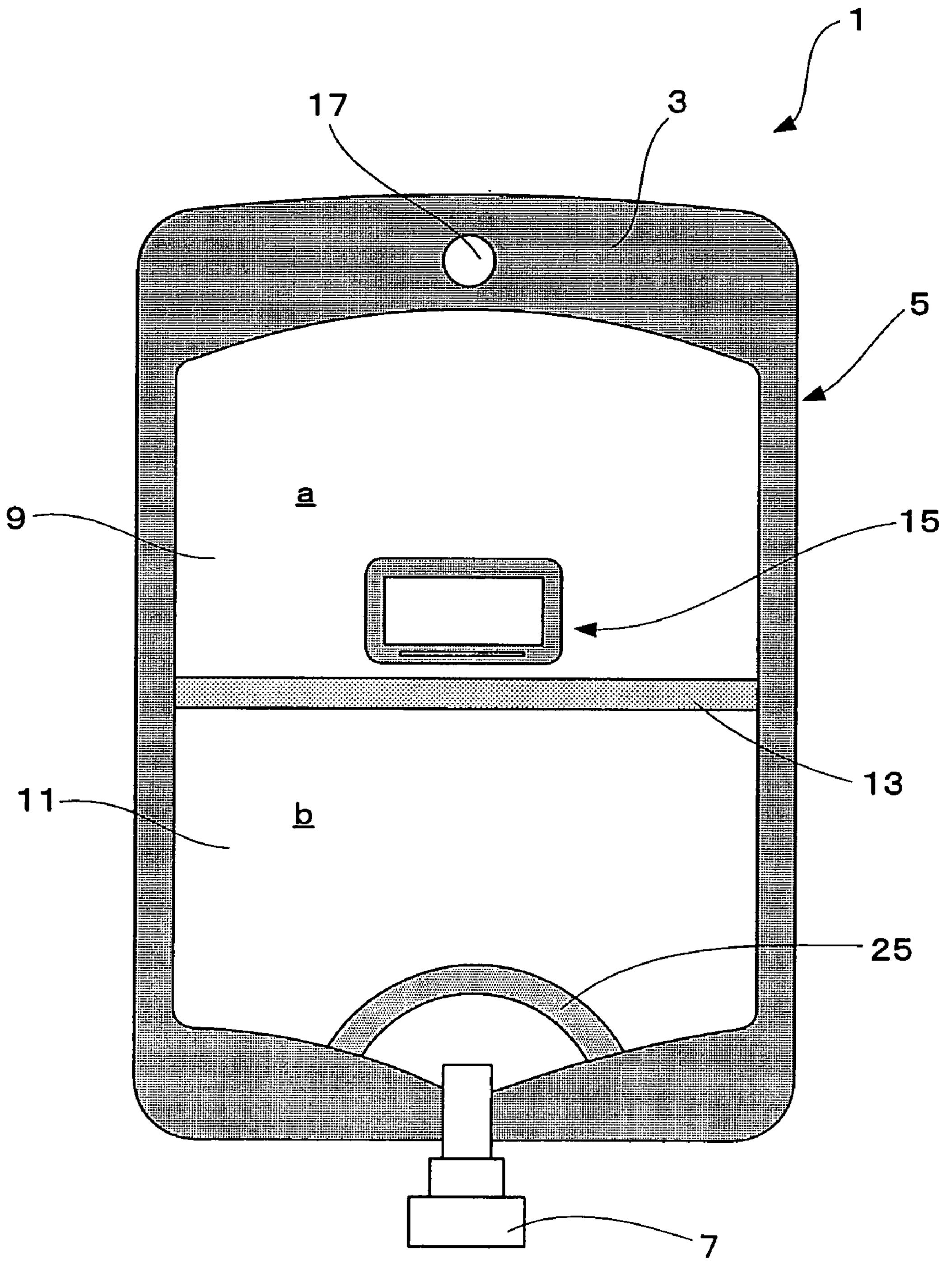
FIG. 9 is a plane view showing a second embodiment of multiple-chamber medical container according to the invention.

With reference to FIG. 9, the multiple-chamber medical container 1 according to the present embodiment is provided with an discharge-control weak seal portion (discharge-control seal portion) 25 serving as a partition between the second chamber 11 and the medicinal outlet portion 7. This discharge-control weak seal portion 25 is in the form of a circular arc surrounding one end of the outlet portion 7 and is formed by heat sealing with substantially the same strength as the partitioning weak seal portion 13.

The discharge-control weak seal portion 25, resembling a circular arc, may be shaped otherwise and is not particularly limited in shape insofar as this portion serves as a partition between the second chamber 11 and the outlet portion 7.

When the container 1 is to be used, the partitioning weak seal portion 13 is opened first to thereby open the small container 15 and mix the medicaments together. The discharge-control weak seal portion 25 is opened next, and the medicinal outlet portion 7 is subsequently pierced with a needle, whereupon the medicinal mixture is run off through the outlet portion 7.

The discharge-control weak seal portion thus provided has the following advantage. Conventionally, if the outlet portion 7 is pierced with a needle in error before the partitioning weak seal portion 13 is opened, there is the likelihood that the medicament within the second chamber 11 will be discharged through the outlet portion 7 before mixing, whereas when the discharge-control weak seal portion 25 is provided, the medicament in the second chamber 11 is blocked by the seal portion 25 and will not be discharged through the outlet portion 7 even if the needle pierces the outlet portion 7 before the partitioning weak seal portion 13 is opened. This directs the worker's attention to the proper method of using the medical container, further making it possible to discharge the medicaments only after mixing.

Figure 10:
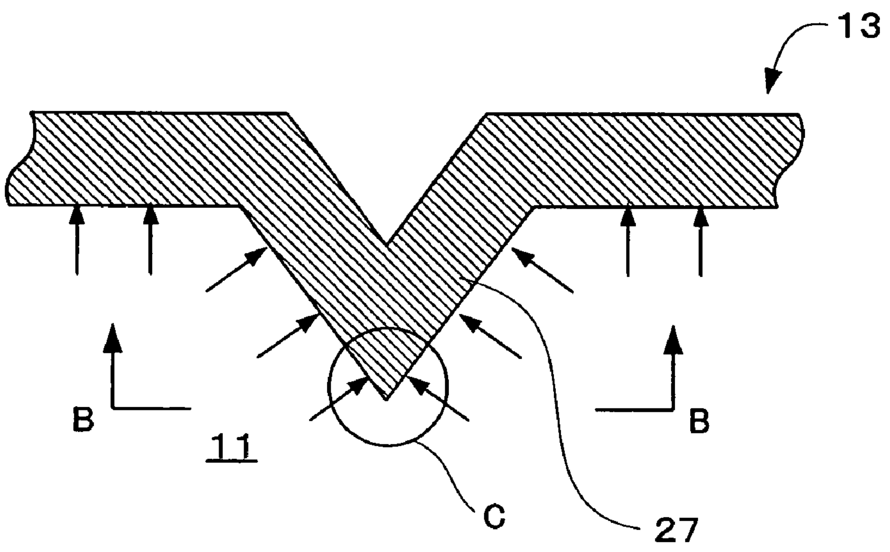
FIG. 10 includes a fragmentary plane view and a view in section which show another example of multiple-chamber medical container of FIG. 6.
Figure 10:
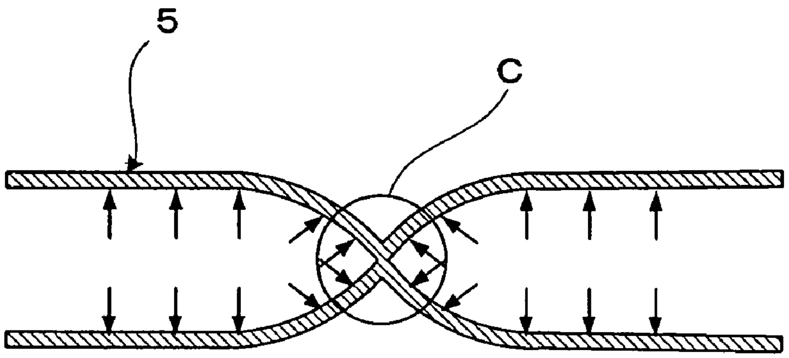

The partitioning weak seal portion 13 and the discharge-control weak seal portion 25 need not always be nearly equivalent in opening strength; one can be lower than the other in strength. One of these portions can be made easier to open than the other, for example, by forming a projection partly on one seal portion. FIG. 10(*a*) shows an example wherein the partitioning weak seal portion 13 is provided at an intermediate part thereof with a V-shaped projection 27. When the second chamber 11 is pressed and thereby given an increased internal pressure as shown in FIG. 10(*b*), the pressure acts on the weak seal portion 13 in the directions of arrows shown. Since equal pressures act on the weak seal portion 13 perpendicular thereto at this time, the total pressure acting on the projection 27 at and around its top C is greater than the pressure in the other region of the weak seal portion 13.

Thus, the pressure acts in such directions as to separate the films forming the container body 5 as shown in FIG. 10(*b*), and the weak seal portion 13 starts to separate first at the top C of the projection 27 when the internal pressure in the chamber 11 further builds up. Consequently, the separation proceeds rapidly under the action of the pressure, opening the partitioning weak seal portion 13 before the discharge-control weak seal portion 25 is opened and thereby causing the first and second chambers 9, 11 to communicate with each other to mix the medicaments. Although not shown, the small container 15 is also opened at the same time.

By providing the projection 27, the two weak seal portions 13, 25 can be made different in opening strength while permitting the weak seal portions 13, 25 to have the same width and the same bond strength. Accordingly, the two seal portions 13, 25 can be formed by heat sealing under the same conditions without the necessity of adjusting the heat-sealing time. This shortens the time required for fabricating the container 1 and results in a reduced production cost.

Besides the discharge-control weak seal portion 25 thus formed, the outlet portion 7 can be provided with a sealed portion for closing the outlet portion 7 on one side thereof closer to the second chamber 11 such that the medicament within the second chamber 11 does not reach the outlet portion 7 unless the sealed portion is subjected to an external force. While the sealed portion thus provided remains closed, the medicament within the second chamber 11 can be prevented from flowing out even if the rubber plug is pieced with the needle.

Third Embodiment

Next, a description will be given of a third embodiment of multiple-chamber medical container according to the present invention. This embodiment differs from the first in that no medicament is accommodated directly in the chamber wherein a small container is disposed. The embodiment otherwise has the same construction as the first and will not be repeatedly described in detail.

Figure 11:
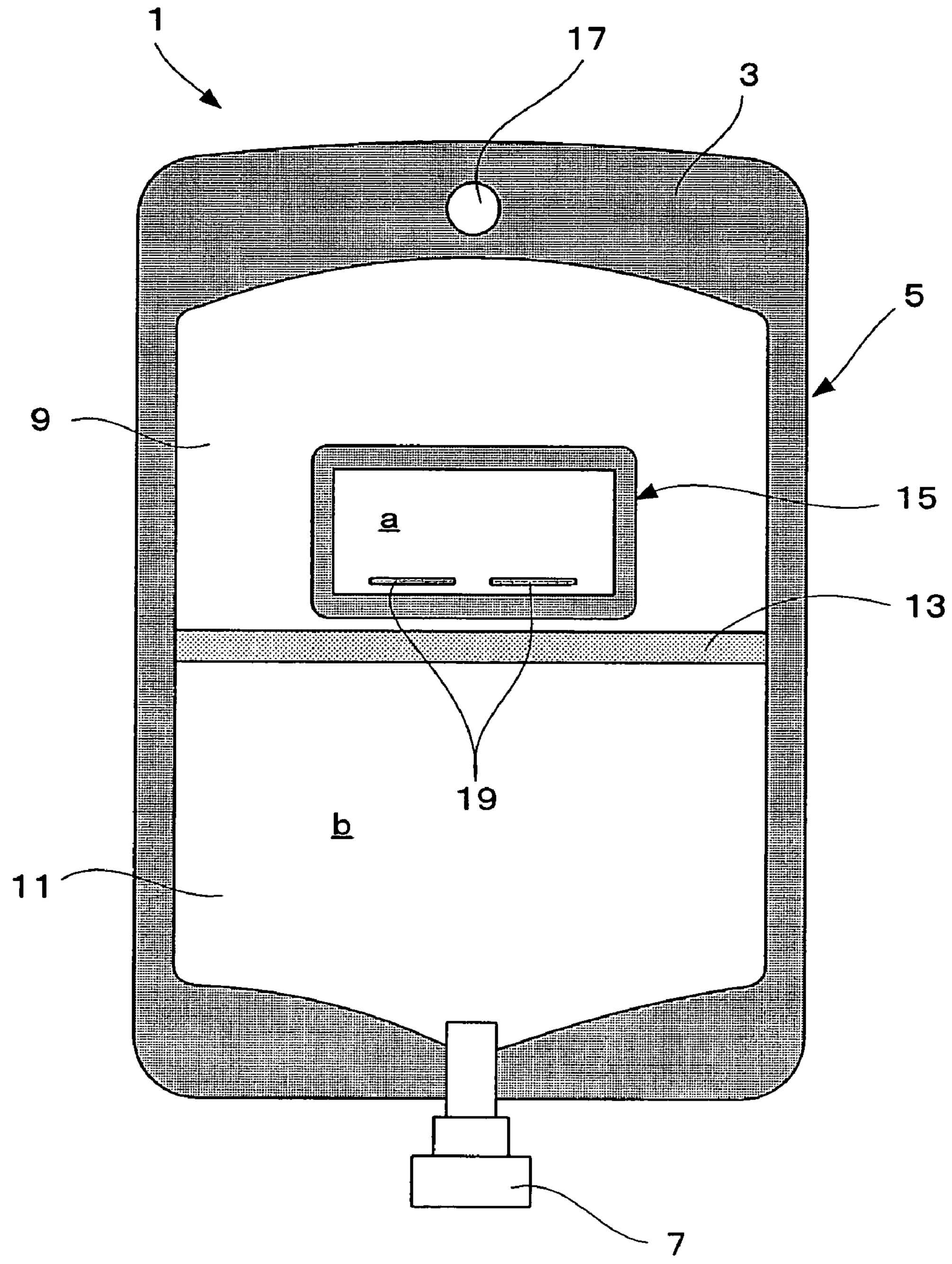
FIG. 11 is a plane view showing a third embodiment of multiple-chamber medical container according to the invention.

With reference to FIG. 11, the medical container of this embodiment has a first chamber 9 wherein the small container 15 alone is disposed, with no medicament accommodated directly therein. On the other hand, a second chamber 11 directly accommodates a liquid medicament b as in the foregoing embodiments. Thus with the present embodiment, no medicament is accommodated directly in the first chamber 9, but the small container 15 enclosing the medicament a therein is placed in the chamber 9, whereby the medicament a is accommodated in the first chamber 9. This results in the following advantage.

In the case where the medicament to be accommodated in the first chamber 9 is altered in quantity, the same container body 5 of unaltered size is made usable merely by using a small container 15 of different size. For example in the case where the medicament to be accommodated in the first chamber 9 is very small in quantity as compared with the size of the chamber, the medicament readily diffuses, so that it is difficult to mix the medicament with the medicament b within the second chamber 11 unless the medicament b is made present over the substantially entire area of the first chamber 9. On the other hand, if the small container 15 is made smaller in size in accordance with the quantity of the medicament a, the medicament can be held present concentrically at one location without diffusing. Accordingly, the medicament a in the small container 15 and the medicament b in the second chamber 11 can be mixed together reliably when the partitioning weak seal portion 13 and the small container 15 are opened.

The present embodiment has another advantage. For example if the medicament a to be placed in the first chamber 9 is likely to be adsorbed by synthetic resins or is susceptible to photo-deterioration, the amount of the medicament a will be decreased or a decomposed product will be formed. In such a case, the small container 15 is formed by films of a material to which the medicament is less likely to be adsorbed or which is less susceptible to photo-deterioration, and is accommodated in the first chamber 9. The small container 15 only can then be of a material suitable for the medicament to be accommodated. This obviates the need to change the material of the entire container body 5 in conformity with the medicament, consequently entailing a cost reduction in the case where such a medicament as described above is to be used.

While it is likely that the medicament a to be enclosed in the small container 15 and the medicament b to be placed into the second chamber 11 of the container body 5 must be different in the method of sterilizing the medicament, the equipment for producing the container body 5 need not be provided with sterilizing equipment for practicing the two sterilizing methods because the small container can be fabricated separately from the container body 5. The medicament a for the small container 9 may be sterilized by the equipment for producing the small container 15, so that the equipment for producing the container body 5 can be provided only with the sterilizing equipment for the medicament for the second chamber 11. The production equipment can therefore be simplified.

Figure 12:
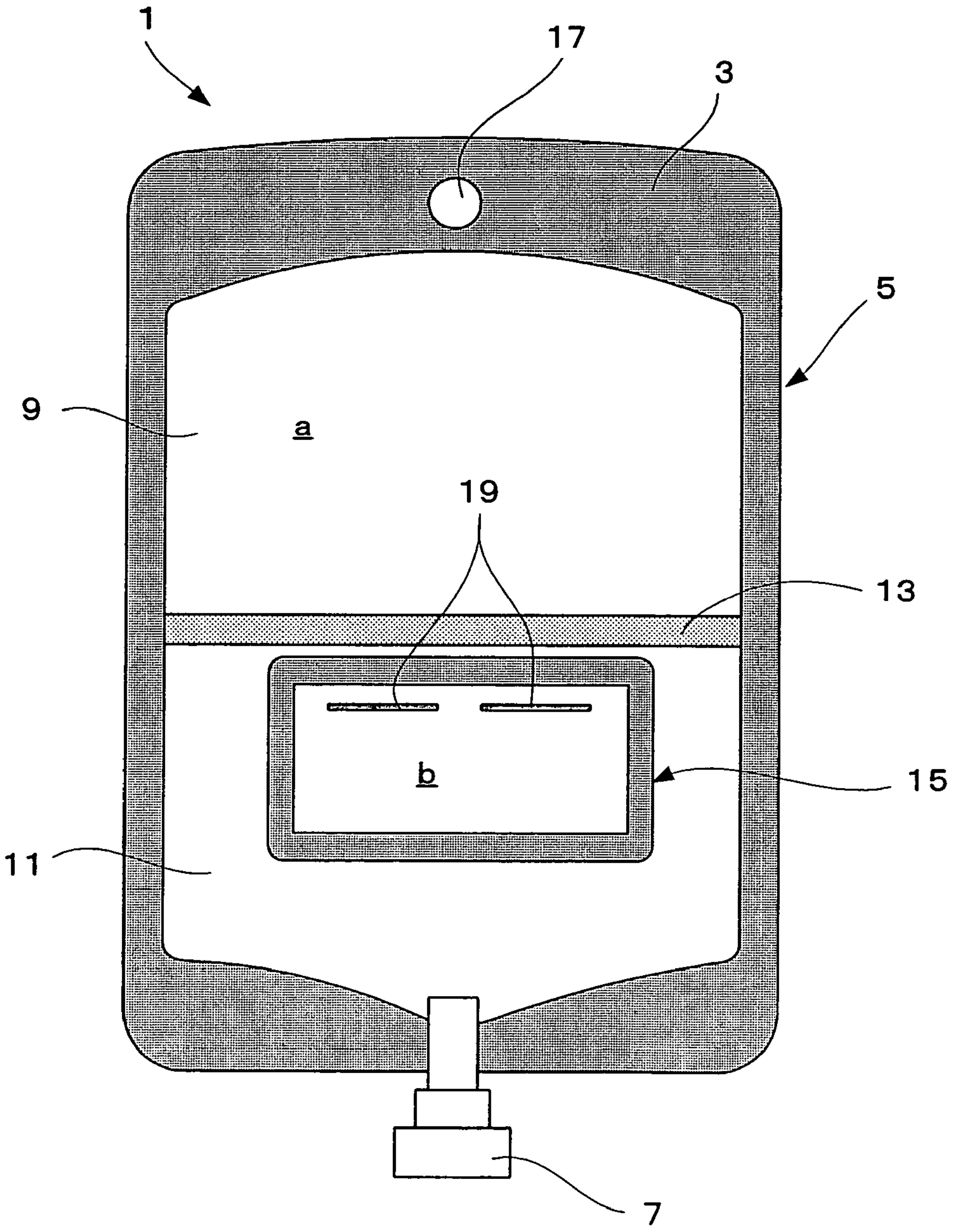
FIG. 12 is a plane view showing another example of the multiple-chamber medical container according to the third embodiment of the invention.

Although the small container 15 is accommodated in the first chamber 9, the small container 15 can be accommodated alternatively in the second chamber 11 as seen in FIG. 12. This arrangement has the following advantage. As shown in the drawing, no medicament is accommodated directly in the second chamber 15, but the small container 11 alone is provided in this chamber. For this reason, no medicament is discharged even if the medicinal outlet portion 7 is pierced with a needle, for example, before the partitioning weak seal portion 13 is opened. Accordingly, the medicaments to be mixed together are prevented from being discharged before mixing. Furthermore, the medicaments can be prevented from being discharged before mixing even in the absence of the discharge-control weak seal portion 25 included in the second embodiment.

As another embodiment, a medicament and the small container 15 can be accommodated in the first chamber 9, with the second chamber 11 left empty. The small container 15 can then be opened easily, while this embodiment has the above advantage of preventing the medicaments from being discharged before mixing.

Figure 13:
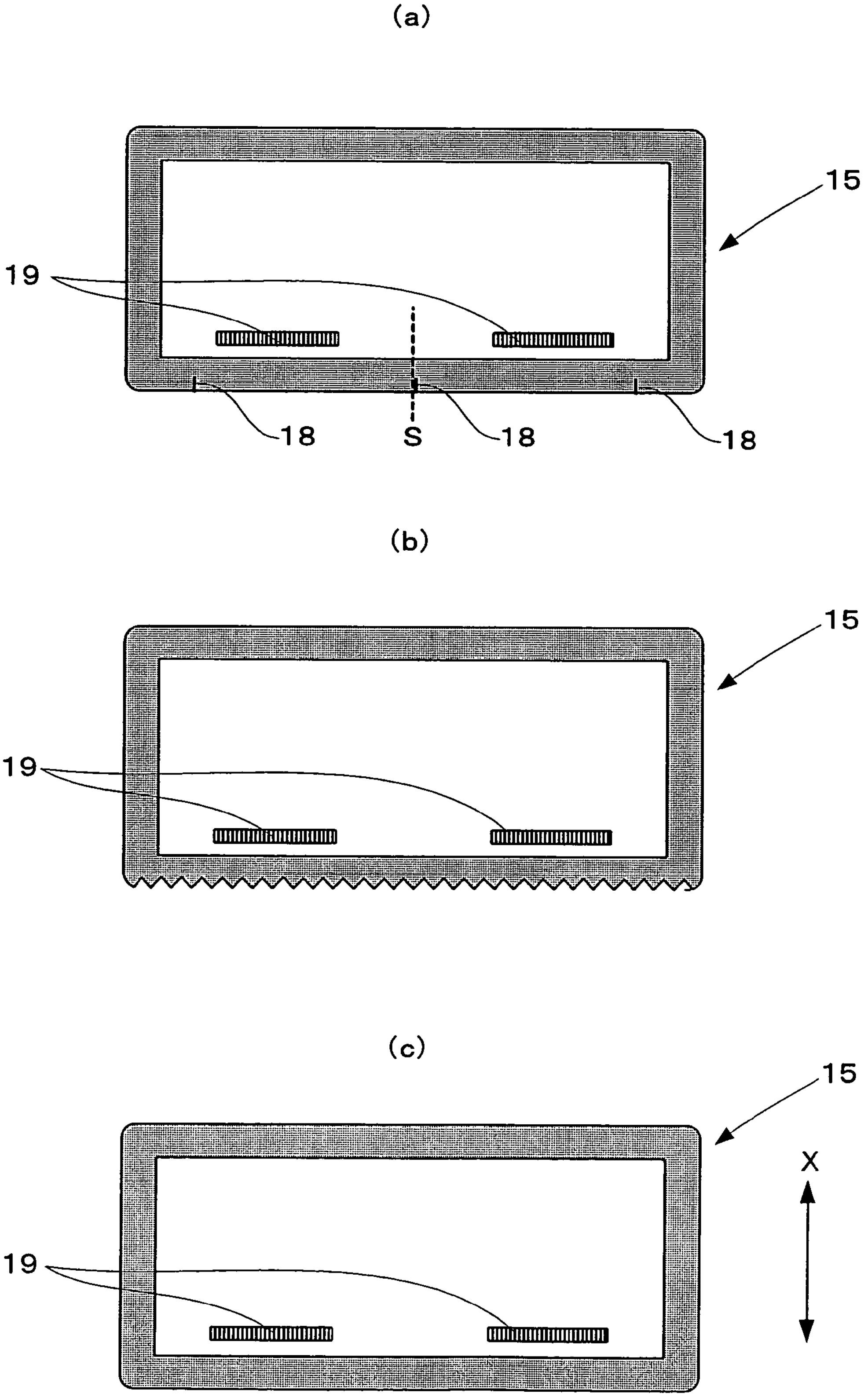
FIG. 13 includes views showing other examples of small containers for use in the multiple-chamber medical container of the invention.
Figure 14:
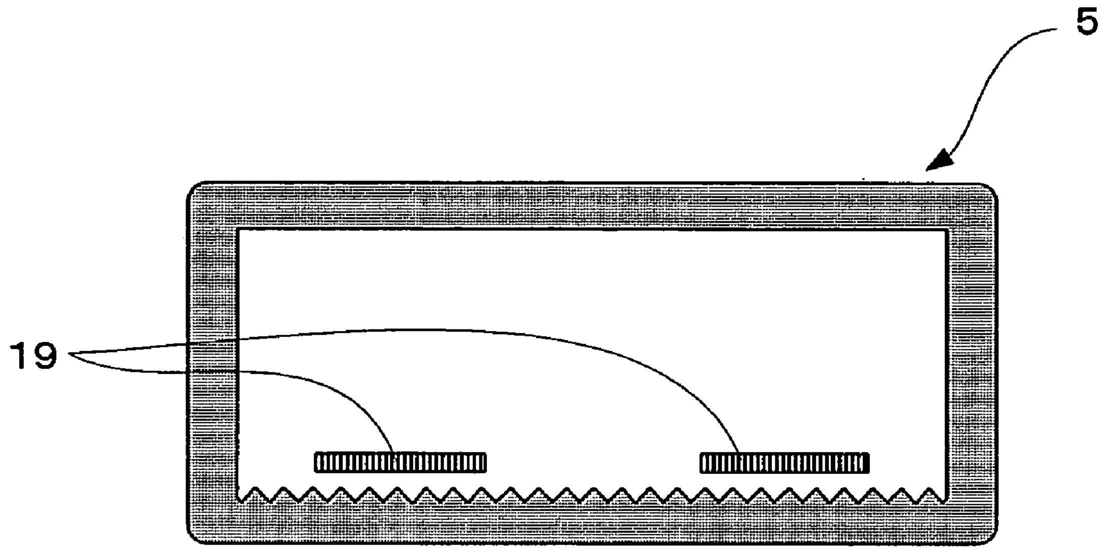
FIG. 14 is a view showing another example of small container for use in the multiple-chamber medical container of the invention.

Although the present invention has been described above with reference to the above embodiments, the invention is not limited to these embodiments but can be modified variously without departing from the gist of the invention. For example, the small containers to be described below can be opened with greater ease. FIG. 13(*a*) shows a plurality of incisions 18 formed in the lower edge of the small container 15. The forces for separating the sheets of the small container 15 can be transmitted to the peripheral edge of the small container 15 through the incisions 18, rendering the peripheral edge liable to break along the line S shown in the drawing. With the peripheral edge thus made easy to break in addition to the delamination of the sheets, the small container 15 can be opened with greater ease. The same effect as above is available also by forming a saw-toothed lower edge 15*a* on the small container 15 as shown in FIG. 13(*b*). Alternatively, when the films for forming the small container 15 are formed by stretching a film material in the directions X shown in FIG. 13(*c*), the films become easy to tear along the direction X. This renders the small container 15 easier to open. Films prepared by a method other than stretching are also usable insofar as they are easy to tear along the direction X. Alternatively, a saw-toothed inner edge can be formed on the periphery of the small container as shown in FIG. 14.

The means described above can be used in a suitable combination to make the small container 15 with further increased ease. More specifically, two or all of the means shown in FIGS. 13(*a*) to 13(*c*) can be used in combination.

Although the partitioning weak seal portion 13 and the discharge-control weak seal portion 25 are formed by heat-sealing films according to the foregoing embodiments, this method is not limitative; the films can be otherwise treated in various modes insofar as they are made openable by applying an external force or forces. For example, the opposed film surfaces of the container body 5 can be provided with a ridge and a furrow, respectively, so as to fit the respective mating the ridge and furrow together separably. Alternatively, a partitioning film can be provided which is locally made smaller in thickness so as to rupture at the thin portion when subjected to a pressure and to cause the two chambers to communicate with each other.

If the small container 15 is fixedly provided in the vicinity of the film in this case, the small container 15 can be opened by separating the films of the container body 5 and thereby causing the two chambers 9, 11 to communicate with each other.

The bonded portion 19 for bonding the small container 15 to the films of the container body 5 need not always be in parallel to the partitioning weak seal portion 13 as previously described, or is not particularly limited in shape insofar as the forces F resulting from the separation of the films of the container body 5 can be delivered to the small container 15. The bonded portion 19, which is formed by heat sealing, can be formed otherwise or is not particularly limited in structure insofar as the small container can be reliably bonded to the container body 5 by the bonded portion.

The small container 15, which is formed by multilayer films or which has a weak seal portion locally in the peripheral edge thereof as described above, can be otherwise constructed insofar as the container 15 is openable by separating the films of the container body 5. For example, the small container 15 can be fabricated in its entirety from thin films which can be ruptured easily.

Furthermore, the small container 15 is not limited to one in number; at least two small containers can be provided. The chamber wherein the small container is disposed is not limited only to the first chamber 9 but can also be the second chamber 11. The small container 15 itself can be divided into a plurality of compartments by a partition or partitions.

The chambers are not limited to two in number as described above but can be at least three. In this case, the chambers may be separated by partitioning weak seal portions like the one already described. The small container may be disposed in at least one of these chambers in the manner described above.

The partitioning seal portion for separating the chambers, which is a weak seal portion formed by heat-sealing the film surfaces according to the embodiments described, can alternatively be a strong seal portion which can be opened by pulling the opposed films of the container body in directions to separate these films. Even the strong seal portion ensures the same advantage as already described, i.e., the advantage that the small container can be opened by opening the strong seal portion.

The invention claimed is:

1. A multiple-chamber medical container comprising:

a container body having multiple chambers for containing medicaments therein and a partitioning seal portion for separating the multiple chambers from one another, a medicinal outlet portion attached to the container body for discharging the medicaments from the chambers therethrough, and an openable additional small container formed of sheet material located within at least one of the multiple chambers and having a medicament enclosed therein;

wherein the partitioning seal portion is formed by separably bonding opposing inner wall surfaces of the container body, the small container is structured to open in response to external force, the small container has a bonded portion bonded to the container body, and the bonded portion comprises opposing outer surfaces of the sheet material, wherein the opposing outer surfaces are each bonded to the opposing inner wall surfaces of the chambers in the vicinity of the partitioning seal portion, and the small container is opened in accordance with the separation of the opposing inner wall surfaces of the container body.

2. A multiple-chamber medical container according to claim 1, wherein the distance between the small container and the partitioning seal portion is 0 to 50 mm.

3. A multiple-chamber medical container according to claim 1 wherein, the small container is heat-sealed at at least one portion of a peripheral edge thereof, the heat-sealed portion is structured to open in response to external force, a nonbonded portion of the small container inwardly of the sealed portion of the peripheral edge has the bonded portion bonded to the container body.

4. A multiple-chamber medical container according to claim 1, wherein the bonded portion of the small container comprises a plurality of bonded parts arranged with at least one nonbonded part positioned therebetween.

5. A multiple-chamber medical container according to claim 4, wherein said at least one nonbonded part is provided in the vicinity of the center of the bonded portion.

6. A multiple-chamber medical container according to claim 1, wherein the sheet material of the small container comprises a multilayer film and the small container is opened by delaminating the multilayer film.

7. A multiple-chamber medical container according to claim 6, wherein the sheet material of the small container comprises a multilayer film formed by laminating a plurality of resin layers having low miscibility with one another.

8. A multiple-chamber medical container according to claim 1, wherein the sheet material of the small container is at least partly heat-sealed, the heat-sealed portion is structured to open in response to an external force.

9. A multiple-chamber medical container according to claim 1, wherein the small container is disposed in at least one of the chambers to thereby accommodate the medicament in the chamber.

10. A multiple-chamber medical container according to claim 9, wherein the medicinal outlet portion is connected to the chamber having the small container disposed therein.

11. A multiple-chamber medical container according to claim 1, wherein a discharge-control seal portion is further provided as an openable partition between the medicinal outlet portion and the chamber.

12. A multiple-chamber medical container according to claim 1, wherein a medicament selected from among an antibiotic, anticancer drug, cardiotonic drug, vitamin and trace element is enclosed in the small container.

13. A multiple-chamber medical container according to claim 1, wherein:

the sheet material of the small container is at least partly heat-sealed;

the heat-sealed portion is structured to open in response to an external force; and the bonded portion is located on the heat-sealed portion.

14. A bag for enclosing therein at least one multiple-chamber medical container according to claim 1, wherein the bonded portion of the small container is provided approximately in parallel to the partitioning seal portion, and the medical container is folded along an edge of the bonded portion on one side thereof opposite to the partitioning seal portion before being placed into the bag.

15. A multiple-chamber medical container comprising:

a container body having multiple chambers for containing medicaments therein and a partitioning seal portion for separating the multiple chambers from one another, a medicinal outlet portion attached to the container body for discharging the medicaments from the chambers therethrough, and an openable additional small container formed of sheet material located within at least one of the multiple chambers and having a medicament enclosed therein;

wherein the partitioning seal portion is formed by separably bonding opposing inner wall surfaces of the container body the small container is structured to open in response to external force, the small container has a bonded portion bonded to the container body, and the bonded portion comprises opposing outer surfaces of the sheet material, wherein the opposing outer surfaces are each bonded to the inner wall surfaces of the partitioning seal portion such that the small container is positioned partly inserted into the partitioning seal portion, and the small container is opened in accordance with the separation of the opposing inner wall surfaces of the container body.

16. A multiple-chamber medical container according to claim 15, wherein the sheet material of the small container comprises a multilayer film and the small container is opened by delaminating the multilayer film.

17. A multiple-chamber medical container according to claim 16, wherein the sheet material of the small container comprises a multilayer film formed by laminating a plurality of resin layers having low miscibility with one another.

18. A multiple-chamber medical container according to claim 15, wherein the sheet material of the small container is at least partly heat-sealed, the heat-sealed portion is structured to open in response to an external force.

19. A multiple-chamber medical container according to claim 15, wherein the small container is disposed in at least one of the chambers to thereby accommodate the medicament in the chamber.

20. A multiple-chamber medical container according to claim 19, wherein the medicinal outlet portion is connected to the chamber having the small container disposed therein.

21. A multiple-chamber medical container according to claim 15, wherein a discharge-control seal portion is further provided as an openable partition between the medicinal outlet portion and the chamber.

22. A multiple-chamber medical container according to claim 15, wherein a medicament selected from among an antibiotic, anticancer drug, cardiotonic drug, vitamin and trace element is enclosed in the small container.

23. A bag for enclosing therein at least one multiple-chamber medical container according to claim 15, wherein the bonded portion of the small container is provided approximately in parallel to the partitioning seal portion, and the medical container is folded along an edge of the bonded portion on one side thereof opposite to the partitioning seal portion before being placed into the bag.

* * * * *